United States Patent
Averback et al.

(10) Patent No.: US 8,067,378 B2
(45) Date of Patent: Nov. 29, 2011

(54) PEPTIDES EFFECTIVE IN THE TREATMENT OF TUMORS AND OTHER CONDITIONS REQUIRING THE REMOVAL OR DESTRUCTION OF CELLS

(75) Inventors: Paul Averback, Beaconsfield (CA); Jack Gemmell, Mississauga (CA)

(73) Assignee: Nymox Pharmaceutical Corporation (CA)

( * ) Notice: Subject to any disclaimer, the term of this patent is extended or adjusted under 35 U.S.C. 154(b) by 807 days.

(21) Appl. No.: 11/680,119

(22) Filed: Feb. 28, 2007

(65) Prior Publication Data

US 2008/0176805 A1    Jul. 24, 2008

Related U.S. Application Data

(60) Provisional application No. 60/776,933, filed on Feb. 28, 2006.

(51) Int. Cl.
*A61K 38/08* (2006.01)
*A61K 38/16* (2006.01)

(52) U.S. Cl. ............... 514/21.8; 514/21.7; 514/21.3; 530/328; 530/325

(58) Field of Classification Search .............. None
See application file for complete search history.

(56) References Cited

U.S. PATENT DOCUMENTS 4,752,602 A * 6/1988 Lipsky et al. ............ 514/19
2004/0214246 A1 * 10/2004 Hoesel et al. ............ 435/7.23
2005/0032704 A1    2/2005 Averback et al.

FOREIGN PATENT DOCUMENTS

| EP | 1541166 | 6/2005 |
| EP | 1564293 | 8/2005 |
| WO | WO 0190194 A2 * | 11/2001 |
| WO | WO-03008444 | 1/2003 |

OTHER PUBLICATIONS

R.V. Talanian et al. J. Biol. Chem. (1997) 272(15), pp. 9677-9682.*

* cited by examiner

*Primary Examiner* — Cecilia J Tsang
*Assistant Examiner* — Satyanarayana Gudibande
(74) *Attorney, Agent, or Firm* — Pillsbury Winthrop Shaw Pittman, LLP; Patrick Doody

(57) ABSTRACT

The embodiments include methods of treating conditions requiring removal or destruction of cellular elements, such as benign or malignant tumors in humans, using compounds based on small peptides. The method includes, but is not limited to, administering the compounds intramuscularly, orally, intravenously, intrathecally, intratumorally, intranasally, topically, transdermally, etc., either alone or conjugated to a carrier.

4 Claims, No Drawings

PEPTIDES EFFECTIVE IN THE TREATMENT OF TUMORS AND OTHER CONDITIONS REQUIRING THE REMOVAL OR DESTRUCTION OF CELLS

CROSS REFERENCE TO RELATED APPLICATION

This application claims benefit of U.S. Provisional Application No. 60/776,933, filed Feb. 28, 2006, which is hereby incorporated by reference in its entirety.

BACKGROUND

1. Field of the Embodiments

The embodiments include methods of treating conditions requiring removal or destruction of cellular elements, such as benign or malignant tumors in humans, using compounds based on small peptides. The method includes, but is not limited to, administering the compounds intramuscularly, orally, intravenously, intrathecally, intratumorally, intranasally, topically, transdermally, etc., either alone or conjugated to a carrier.

2. Description of Related Art

The essence of many medical treatments and procedures involves the removal or destruction of harmful or unwanted tissue. Examples of such important treatments include the surgical removal of cancerous growths, the destruction of metatastic tumors through chemotherapy, and the reduction of glandular (e.g. prostate) hyperplasia. Other examples include the removal of unwanted facial hair, the removal of warts, and the removal of unwanted fatty tissue.

There is an obvious need for an effective agent that will destroy and hence either facilitate the removal of or inhibit the further growth of harmful or unwanted cells and tissue but will have mainly local effects and minimal or absent systemic toxicity.

Classes of such agents are disclosed in pending U.S. patent application Ser. No. 10/092,934, entitled: Methods of Treating Tumors and Related Conditions Using Neural Thread Proteins, Ser. No. 10/153,334, entitled: Peptides Effective In The Treatment Of Tumors And Other Conditions Requiring The Removal Or Destruction Of Cells; Ser. No. 10/198,069, entitled: Peptides Effective In The Treatment Of Tumors And Other Conditions Requiring The Removal Or Destruction Of Cells; Ser. No. 10/198,070, entitled: Peptides Effective In The Treatment Of Tumors And Other Conditions Requiring The Removal Or Destruction Of Cells, Ser. No. 10/294,891 entitled: Peptides Effective In The Treatment Of Tumors And Other Conditions Requiring The Removal Or Destruction Of Cells; and Ser. No. 10/920,313 entitled: Peptides Effective In The Treatment Of Tumors And Other Conditions Requiring The Removal Or Destruction Of Cells, the disclosures of each of which are incorporated by reference herein in their entirety.

Disclosed herein are composites, fragments and subsequences of one such peptide agent (SEQ ID NO. 1: Ile-Asp-Gln-Gln-Val-Leu-Ser-Arg-Ile-Lys-Leu-Glu-Ile-Lys-Arg-Cys-Leu) that also are useful in treating tumors and other conditions requiring removal or destruction of cells.

Cancer is an abnormality in a cell's internal regulatory mechanisms that results in uncontrolled growth and reproduction of the cell. Normal cells make up tissues, and when these cells lose their ability to behave as a specified, controlled, and coordinated unit, (dedifferentiation), the defect leads to disarray amongst the cell population. When this occurs, a tumor is formed.

Benign overgrowths of tissue are abnormalities in which it is desirable to remove cells from an organism. Benign tumors are cellular proliferations that do not metastasize throughout the body but do, however, cause disease symptoms. Such tumors can be lethal if they are located in inaccessible areas in organs such as the brain. There are benign tumors of organs including lung, brain, skin, pituitary, thyroid, adrenal cortex and medulla, ovary, uterus, testis, connective tissue, muscle, intestines, ear, nose, throat, tonsils, mouth, liver, gall bladder, pancreas, prostate, heart, and other organs.

Surgery often is the first step in the treatment of cancer. The objective of surgery varies. Sometimes it is used to remove as much of the evident tumor as possible, or at least to "debulk" it (remove the major bulk(s) of tumor so that there is less that needs to be treated by other means). Depending on the cancer type and location, surgery may also provide some symptomatic relief to the patient. For instance, if a surgeon can remove a large portion of an expanding brain tumor, the pressure inside the skull will decrease, leading to improvement in the patient's symptoms.

Not all tumors are amenable to surgery. Some may be located in parts of the body that make them impossible to completely remove. Examples of these would be tumors in the brainstem (a part of the brain that controls breathing) or a tumor which has grown in and around a major blood vessel. In these cases, the role of surgery is limited due to the high risk associated with tumor removal.

In some cases, surgery is not used to debulk tumor because it is simply not necessary. An example is Hodgkin's lymphoma, a cancer of the lymph nodes that responds very well to combinations of chemotherapy and radiation therapy. In Hodgkin's lymphoma, surgery is rarely needed to achieve cure, but almost always used to establish a diagnosis.

Chemotherapy is another common form of cancer treatment. Essentially, it involves the use of medications (usually given by mouth or injection) which specifically attack rapidly dividing cells (such as those found in a tumor) throughout the body. This makes chemotherapy useful in treating cancers that have already metastasized, as well as tumors that have a high chance of spreading through the blood and lymphatic systems but are not evident beyond the primary tumor. Chemotherapy may also be used to enhance the response of localized tumors to surgery and radiation therapy. This is the case, for example, for some cancers of the head and neck.

Unfortunately, other cells in the human body that also normally divide rapidly (such as the lining of the stomach and hair) also are affected by chemotherapy. For this reason, many chemotherapy agents induce undesirable side effects such as nausea, vomiting, anemia, hair loss or other symptoms. These side effects are temporary, and there exist medications that can help alleviate many of these side effects. As our knowledge has continued to grow, researchers have devised newer chemotherapeutic agents that are not only better at killing cancer cells, but that also have fewer side effects for the patient.

Chemotherapy is administered to patients in a variety of ways. Some include pills and others are administered by an intravenous or other injection. For injectable chemotherapy, a patient goes to the doctor's office or hospital for treatment. Other chemotherapeutic agents require continuous infusion into the bloodstream, 24 hours a day. For these types of chemotherapy, a minor surgical procedure is performed to implant a small pump worn by the patient. The pump then slowly administers the medication. In many cases, a permanent port is placed in a patient's vein to eliminate the requirement of repeated needle sticks.

Radiation therapy is another commonly used weapon in the fight against cancer. Radiation kills cancer by damaging the DNA within the tumor cells. The radiation is delivered in different ways. The most common involves pointing a beam of radiation at the patient in a highly precise manner, focusing on the tumor. To do this, a patient lies on a table and the beam moves around him/her. The procedure lasts minutes, but may be done daily for several weeks (depending on the type of tumor), to achieve a particular total prescribed dose.

Another radiation method sometimes employed, called brachytherapy, involves taking radioactive pellets (seeds) or wires and implanting them in the body in the area of the tumor. The implants can be temporary or permanent. For permanent implants, the radiation in the seeds decays over a period of days or weeks so that the patient is not radioactive. For temporary implants, the entire dose of radiation is usually delivered in a few days, and the patient must remain in the hospital during that time. For both types of brachytherapy, radiation is generally delivered to a very targeted area to gain local control over a cancer (as opposed to treating the whole body, as chemotherapy does.)

Some highly selected patients may be referred for bone marrow transplants. This procedure usually is performed either because a patient has a cancer that is particularly aggressive or because they have a cancer that has relapsed after being treated with conventional therapy. Bone marrow transplantation is a complicated procedure. There are many types, and they vary in their potential for causing side effects and cure. Most transplants are performed at special centers, and in many cases, their use is considered investigational.

A number of other therapies exist, although most of them are still being explored in clinical trials and have not yet become standard care. Examples include the use of immunotherapy, monoclonal antibodies, anti-angiogenesis factors and gene therapy.

Immunotherapy: There are various techniques designed to help the patient's own immune system fight the cancer, quite separately from radiation or chemotherapy. Oftentimes, to achieve the goal researchers inject the patient with a specially derived vaccine.

Monoclonal Antibodies: These are antibodies designed to attach to cancerous cells (and not normal cells) by taking advantage of differences between cancerous and non-cancerous cells in their antigenic and/or other characteristics. The antibodies can be administered to the patient alone or conjugated to various cytotoxic compounds or in radioactive form, such that the antibody preferentially targets the cancerous cells, thereby delivering the toxic agent or radioactivity to the desired cells.

Anti-Angiogenesis Factors: As cancer cells rapidly divide and tumors grow, they can soon outgrow their blood supply. To compensate for this, some tumors secrete a substance believed to help induce the growth of blood vessels in their vicinity, thus providing the cancer cells with a vascular source of nutrients. Experimental therapies have been designed to arrest the growth of blood vessels to tumors.

Gene Therapy: Cancer is the product of a series of mutations that ultimately lead to the production of a cancer cell and its excessive proliferation. Cancers can be treated by introducing genes to the cancer cells that will act either to check or stop the cancer's proliferation, turn on the cell's programmed cell mechanisms to destroy the cell, enhance immune recognition of the cell, or express a pro-drug that converts to a toxic metabolite or a cytokine that inhibits tumor growth.

Benign tumors and malformations also can be treated by a variety of methods including surgery, radiotherapy, drug therapy, thermal or electric ablation, cryotherapy, and others. Although benign tumors do not metastasize, they can grow large and they can recur. Surgical extirpation of benign tumors has all the difficulties and side effects of surgery in general and oftentimes must be repeatedly performed for some benign tumors, such as for pituitary adenomas, meningeomas of the brain, prostatic hyperplasia, and others.

Other conditions involving unwanted cellular elements exist where selective cellular removal is desirable. For example, heart disease and strokes commonly are caused by atherosclerosis, which is a proliferative lesion of fibrofatty and modified smooth muscle elements that distort the blood vessel wall, narrow the lumen, constrict blood flow, predispose to focal blood clots, and ultimately lead to blockage and infarction. There are various treatments for atherosclerosis such as bypass grafts; artificial grafts; angioplasty with recanalization, curettage, radiation, laser, or other removal; pharmacotherapy to inhibit atherosclerosis through lipid reduction; anti-clotting therapies; and general measures of diet, exercise, and lifestyle. A method for removing atherosclerotic lesions without the risk and side effects of surgical procedures is needed.

Other examples of unwanted cellular elements where selective cellular removal is desirable include viral induced growths, such as warts. Another example is hypertrophic inflammatory masses found in inflammatory conditions, and hypertrophic scars or keloids. Still other examples are found in cosmetic contexts such as the removal of unwanted hair, e.g., facial hair, or for shrinkage of unwanted tissue areas for cosmetic purposes, such as in the facial dermis and connective tissues or in the dermas and connective tissue of the extremities.

Other examples of unwanted cellular elements where selective cellular removal or the inhibition of cellular proliferation is desirable include stenosis and restenosis of any artery, valve or canal in the circulatory system including, but not limited to, valves (e.g., aortic stenosis which involves narrowing of the aortic valve orifice), coronary arteries (e.g., coronary ostial sclerosis which involves narrowing of the mouths of the coronary arteries), carotid arteries, and renal arteries. Other examples include the inhibition or removal of unwanted cellular growth or accumulation causing the partial or complete occlusion of medical devices such as stents placed or implanted within a blood vessel for treating stenoses, strictures or aneurysms therein or within the urinary tract and in bile ducts.

Still other examples will be obvious to those of ordinary skill in the art. In all or most of these examples there is a need for treatments that can remove or destroy the unwanted cellular elements without the risks and side effects of conventional therapies or remove the unwanted cellular elements with more precision.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending U.S. patent applications, are prior art to the present disclosure. Moreover, the description herein of any disadvantages associated with the described products, methods, and/or apparatus, is not intended to limit the embodiments. Indeed, aspects of the embodiments may include certain features of the described products, methods, and/or apparatus without suffering from their described disadvantages.

SUMMARY OF THE EMBODIMENTS

There remains a need in the art for new, less toxic treatments for treating unwanted cellular elements. The embodiments satisfies these needs.

This disclosure is premised in part on the discovery that certain peptides, including a specific peptide described by the amino acid sequence Ile-Asp-Gln-Gln-Val-Leu-Ser-Arg-Ile-Lys-Leu-Glu-Ile-Lys-Arg-Cys-Leu (SEQ ID NO: 1), are capable of treating and/or killing unwanted cellular proliferations. These unwanted cellular proliferations include, inter alia, benign and malignant tumors, glandular (e.g. prostate) hyperplasia, unwanted facial hair, warts, and unwanted fatty tissue.

The embodiments described herein are premised in part on the surprising and unexpected discovery that certain peptide fragments and subsequences of the peptide Ile-Asp-Gln-Gln-Val-Leu-Ser-Arg-Ile-Lys-Leu-Glu-Ile-Lys-Arg-Cys-Leu (SEQ ID NO: 1)("S05A Peptides") also have the capability of treating and/or killing unwanted cellular proliferations.

Some embodiments are directed to methods of treating unwanted cellular proliferations (benign and malignant tumors, glandular (e.g. prostate) hyperplasia, unwanted facial hair, warts, and unwanted fatty tissue) comprising administering to a mammal in need thereof a therapeutically effective amount of an S05A Peptide.

Such an S05A Peptide can be administered alone or conjugated to a carrier or an antibody. The S05A Peptides can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc., either alone or conjugated to a carrier. Alternatively, the S05A Peptides can be expressed in vivo by administering a gene that expresses the S05A Peptides, by administering a vaccine that induces such production or by introducing cells, bacteria or viruses that express the peptide in vivo, because of genetic modification or otherwise.

In addition, the S05A Peptides may be used in conjunction with other therapies for treating benign and malignant tumors and other unwanted or harmful cellular growths.

Both the foregoing general description and the following detailed description are exemplary and explanatory and are intended to provide further explanation of the embodiments as claimed. Other objects, advantages, and features will be readily apparent to those skilled in the art from the following detailed description of the embodiments.

DETAILED DESCRIPTION OF THE PREFERRED EMBODIMENTS

Before the present proteins, nucleotide sequences, peptides, etc., and methods are described, it is understood that this invention is not limited to the particular methodology, protocols, cell lines, vectors, and reagents described, as these may vary. It also is to be understood that the terminology used herein is for the purpose of describing particular embodiments only, and is not intended to limit the scope of the present embodiments which will be limited only by the appended claims.

Terms and phrases used herein are defined as set forth below unless otherwise specified.

Throughout this description, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Amino acids and amino acid residues described herein may be referred to according to the accepted one or three-letter code provided in the table below.

TABLE 1

| Three-Letter Amino Acid | One-Letter Symbol | Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The term "peptide" as it is used herein, refers to a chain of at least two amino acids and includes homologues, derivatives, fragments, and variants of the peptide. The expression "S05A Peptide" refers to a peptide comprising at least one fragment or subsequence of the peptide SEQ ID NO. 1 (Ile-Asp-Gln-Gln-Val-Leu-Ser-Arg-Ile-Lys-Leu-Glu-Ile-Lys-Arg-Cys-Leu) and includes any homologue, fragment, derivative, variant, fusion protein, and peptide mimetics of the peptide unless the context indicates otherwise. The expression "S05A Peptides" includes (but is not limited to) peptides comprising at least one peptide selected from the group consisting of:

a) the peptide represented by the amino acid sequence in SEQ ID NO. 2 (Ile-Asp-Gln-Gln-Val-Leu-Ser-Arg-Ile);
b) the peptide represented by the amino acid sequence in SEQ ID NO. 3 (Lys-Leu-Glu-Ile-Lys-Arg-Cys-Leu);
c) the peptide represented by the amino acid sequence in SEQ ID NO. 4 (Val-Leu-Ser-Arg-Ile-Lys);
d) the peptide represented by the amino acid sequence in SEQ ID NO. 5 (Arg-Ile-Lys-Leu-Glu-Ile-Lys);
e) the peptide represented by the amino acid sequence in SEQ ID NO. 6 (Val-Leu-Ser-Arg-Ile-Lys-Leu-Glu-Ile-Lys-Arg-Cys-Leu); and
f) the peptide represented by the amino acid sequence in SEQ ID NO. 7 (Ile-Asp-Gln-Gln-Val-Leu-Ser-Arg-Ile-Lys-Leu-Glu-Ile).

The term "fragment" or "subsequence" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. As a consequence, any peptide that includes a fragment of SEQ ID NO. 1 can be any of those selected above, as well as other fragments or subsequences that, while not delineated herein for purposes of brevity, will be readily apparent to those skilled in the art. The skilled artisan also will be capable of selecting a suitable fragment for use in the embodiments without undue experimentation using the guidelines and procedures outlined herein.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, Sequence Analysis in Molecular Biology, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

Conservative Amino Acid Substitutions

| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | praline |
| | methionine |
| | leucine |
| | isoleucine |

Table 3 sets out another scheme of amino acid substitution:

TABLE 3

| Original Residue | Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | eu; val |
| Leu | ile; val |
| Lys | arg; gln; glu |
| Met | leu; tyr; ile |
| Phe | met; leu; tyr |
| Ser | thr |
| Thr | ser |

TABLE 3-continued

| Original Residue | Substitutions |
|---|---|
| Trp | tyr |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. For example, a cysteine residue may be added at both the amino and carboxy terminals of an S05A Peptide in order to allow the cyclisation of the Peptide by the formation of a di-sulphide bond. The term "variant" also encompasses polypeptides that have the amino acid sequence of an S05A Peptide with at least one and up to 25 or more additional amino acids flanking either the 3' or 5' end of the Peptide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins or S05A Peptides. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, 2nd Ed., T. E. Creighton, W. H. Freeman and Company, New York (1993) and Wold, F., "Posttranslational Protein Modifications: Perspectives and Prospects," pgs. 1-12 in Posttranslational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 60 percent identical in its amino acid sequence of an S05A Peptide as determined by standard methods that are commonly used to compare the similarity in position of the amino acids of two polypeptides. The degree of similarity or identity between two proteins can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M Stockton Press, New York, 1991; and Carillo H. and Lipman, D., SIAM, J. Applied Math., 48:1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., Nucleic Acids Research, 12(1): 387 (1984)), BLASTP, BLASTN, and FASTA, Atschul, S. F. et al., J. Molec. Biol., 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol., 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al. in: Atlas of Protein Sequence and Structure, vol. 5, supp.3 for the PAM250 comparison matrix; see Henikoff et al., Proc. Natl. Acad. Sci. USA, 89:10915-10919 for the BLOSUM 62 comparison matrix) also may be used by the algorithm. The percent identity then is calculated by the algorithm. Homologues will typically have one or more amino acid substitutions, deletions, and/or insertions as compared with the comparison protein or peptide, as the case may be.

The term "fusion protein" refers to a protein where one or more peptides are recombinantly fused or chemically conjugated (including covalently and non-covalently) to a protein such as (but not limited to) an antibody or antibody fragment like an F.sub.ab fragment or short chain Fv. The term "fusion protein" also refers to multimers (i.e. dimers, trimers, tetramers and higher multimers) of peptides. Such multimers comprise homomeric multimers comprising one peptide, heteromeric multimers comprising more than one peptide, and heteromeric multimers comprising at least one peptide and at least one other protein. Such multimers may be the result of hydrophobic, hydrophilic, ionic and/or covalent associations, bonds or links, may be formed by cross-links using linker molecules or may be linked indirectly by, for example, liposome formation The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments are preferably substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala.sup.1-Peptide T Binding", Smith C. S. et al., Drug Development Res., 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the peptide by pseudopeptide bonds that. confer resistance to proteolysis.

A number of pseudopeptide bonds have been described that in general do not affect peptide structure and biological activity. One example of this approach is to substitute retroinverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of an peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), Int. J. Peptide Protein Res., 41:181-184, incorporated herein by reference in its entirety).

Thus, the amino acid sequences of these peptides may be identical to the sequences of an peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of peptides represent another class of peptide mimetics that retain the important structural determinants for biological activity, yet eliminate the peptide bonds, thereby conferring resistance to proteolysis (Simon, et al., 1992, Proc. Natl. Acad. Sci. USA, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the peptides may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of an peptide. Thus, the carboxy terminal residue of an L-amino acid peptide becomes the amino terminal for the D-amino acid peptide and so forth. For example, the peptide ETESH (SEQ ID NO: 8), becomes $H_dS_dE_dT_dE_d$, where $E_d$, $H_d$, $S_d$, and $T_d$ are the D-amino acids corresponding to the L-amino acids, E, H, S, and T respectively.

The term "enantiomer" refers to a biologically active protein or peptide where one or more the L-amino acid residues in the amino acid sequence of an peptide is replaced with the corresponding D-amino acid residue(s).

A "composition" as used herein, refers broadly to any composition containing a recited peptide or amino acid sequence. The composition may comprise a dry formulation, an aqueous solution, or a sterile composition. Compositions comprising peptides may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

The embodiments are directed to a composition comprising S05A Peptides as defined above in this embodiment.

Moreover, the embodiments includes other proteins that contain in whole or part an S05A Peptide, whereby the proteins preferably possess the same, similar, or enhanced bioactivity as the Peptide. Using the guidelines provided herein, a person ordinarily skilled in the art could synthesize specific proteins based on the amino acid sequence for any S05A Peptide found to be an effective agent for causing cell death and test them for efficacy as agents for causing cell death.

Other peptide sequences derived from an S05A Peptide found to be an effective agent for causing cell death also may be effective agents for causing cell death. A person ordinarily skilled in the art can, using the guidelines provided herein, synthesize without undue experimentation fragments of an effective Peptide spanning the entire amino acid sequence of that protein in order to identify other effective peptide sequences.

The S05A Peptides of the particularly preferred embodiments include, but are not limited to, the following:

```
                                           SEQ ID NO. 2
IDQQVLSRI  Ile-Asp-Gln-Gln-Val-Leu-Ser-Arg-Ile

SEQ ID NO. 3
KLEIKRCL   Lys-Leu-Glu-Ile-Lys-Arg-Cys-Leu

SEQ ID NO. 4
VLSRIK     Val-Leu-Ser-Arg-Ile-Lys

SEQ ID NO. 5
RIKLEIK    Arg-Ile-Lys-Leu-Glu-Ile-Lys

SEQ ID NO. 6
VLSRIKLEIKRCL  Val-Leu-Ser-Arg-Ile-Lys-Leu-Glu-Ile-
Lys-Arg-Cys-Leu

SEQ ID NO. 7
IDQQVLSRIKLEI  Ile-Asp-Gln-Gln-Val-Leu-Ser-Arg-Ile-
Lys-Leu-Glu-Ile
```

It will be apparent to one of skill in the art that other smaller fragments of the above S05A Peptides may be selected such that these peptides will possess the same or similar biological activity. Other fragments of may be selected by one skilled in the art such that these peptides will possess the same or similar biological activity. The peptides of the embodiments encompass these other fragments. In general, the peptides of the embodiments have at least 6 amino acids, preferably at least 5 amino acids, and more preferably at least 4 amino acids.

The embodiments also encompasses S05A Peptides comprising two or more S05A Peptides joined together. To the extent that an S05A Peptide has the desired biological activity, it follows that two such Peptides would also possess the desired biological activity.

S05A Peptides and fragments, variants, derivatives, homologues, fusion proteins and mimetics thereof encompassed by this embodiment can be prepared using methods known to those of skill in the art, such as recombinant DNA technology, protein synthesis and isolation of naturally occurring peptides, proteins, AD7c-protein and fragments, variants, derivatives and homologues thereof.

S05A Peptides and fragments, variants, derivatives, homologues, fusion proteins and mimetics thereof can be prepared from other peptides, proteins, and fragments, variants, derivatives and homologues thereof using methods known to those having skill in the art. Such methods include (but are not limited to) the use of proteases to cleave the peptide, or protein into the desired S05A Peptides.

An S05A Peptide can be prepared using well known recombinant DNA technology methods such as those set forth in Sambrook et al. Molecular Cloning: A Laboratory Manual, Cold Spring Harbor Laboratory Press, Cold Spring Harbor, N.Y. and/or Ausubel et al., eds., Current Protocols in Molecular Biology, Green Publishers Inc. and Wiley and Sons, N.Y.

A gene or cDNA encoding an S05A Peptide may be obtained for example by screening a genomic or cDNA library, or by PCR amplification. Probes or primers useful for screening the library can be generated based on sequence information for other known genes or gene fragments from the same or a related family of genes, such as, for example, conserved motifs found in other peptides or proteins. In addition, where a gene encoding an S05A Peptide has been identified, all or a portion of that gene may be used as a probe to identify homologous genes. The probes or primers may be used to screen cDNA libraries from various tissue sources believed to express an S05A Peptide gene. Typically, conditions of high stringency will be employed for screening to minimize the number of false positives obtained from the screen.

Another means to prepare a gene encoding an S05A Peptide is to employ chemical synthesis using methods well known to the skilled artisan, such as those described by Engels et al., Angew. Chem. Intl. Ed., 28:716-734. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding an peptide or protein will be several hundred nucleotides in length. Nucleic acids larger than about 100 to nucleotides can be synthesized as several fragments using these methods. The fragments then can be ligated together to form the full length peptide or protein. Usually, the DNA fragment encoding the amino terminus of the protein will have an ATG, which encodes a methionine residue. This methionine may or may not be present on the mature form of the protein or peptide, depending on whether the protein produced in the host cell is designed to be secreted from that cell.

The gene, cDNA, or fragment thereof encoding the S05A Peptide can be inserted into an appropriate expression or amplification vector using standard ligation techniques. The vector is typically selected to be functional in the particular host cell employed (i.e., the vector is compatible with the host cell machinery such that amplification of the gene and/or expression of the gene can occur). The gene, cDNA or fragment thereof encoding the S05A Peptide may be amplified/expressed in prokaryotic, yeast, insect (baculovirus systems) and/or eukaryotic host cells. Selection of the host cell will depend in part on whether the S05A Peptide is to be glycosylated and/or phosphorylated. If so, yeast, insect, or mammalian host cells are preferable.

Typically, the vectors used in any of the host cells will contain at least 5' flanking sequence (also referred to as a promoter) and other regulatory elements as well, such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below.

Optionally, the vector may contain a tag sequence, i.e., an oligonucleotide molecule located at the 5' or 3' end of the protein or peptide coding sequence; the oligonucleotide molecule encodes poly His (such as hexaHis (SEQ ID NO: 9)), or other tag such as FLAG, HA (hemaglutinin Influenza virus) or myc for which commercially available antibodies exist. This tag is typically fused to the polypeptide upon expression of the polypeptide, and can serve as means for affinity purification of the protein or peptide from the host cell. Affinity purification can be accomplished, for example, by column chromatography using antibodies against the tag as an affinity matrix. Optionally, the tag can subsequently be removed from the purified protein or peptide by various means such as using certain peptidases.

The human immunoglobulin hinge and Fc region could be fused at either the N-terminus or C-terminus of the S05A Peptide by one skilled in the art. The subsequent Fc-fusion protein could be purified by use of a Protein A affinity column. Fc is known to exhibit a long pharmacokinetic half-life in vivo and proteins fused to Fc have been found to exhibit a substantially greater half-life in vivo than the unfused counterpart. Also, fusion to the Fc region allows for dimerization/multimerization of the molecule that may be useful for the bioactivity of some molecules.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native protein or peptide gene 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this embodiment may be obtained by any of several methods well known in the art. Typically, 5' flanking sequences useful herein other than the protein or peptide gene flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the protein or peptide. If the vector of choice does not contain an origin of replication site, one may be chemically synthesized based on a known sequence, and ligated into the vector. The transcription termination element is typically located 3' of the end of the protein or peptide coding sequence and serves to terminate transcription of the protein or peptide. Usually, the transcription termination element in prokaryotic cells is a G-C rich fragment followed by a poly T sequence. While the element may be cloned from a library or purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translation initiation of mRNA. The element is typically located 3' to the promoter and 5' to the coding sequence of the protein or peptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for an S05A Peptide to be secreted from the host cell, a signal sequence may be used to direct the Peptide out of the host cell where it is synthesized, and the carboxy-terminal part of the protein may be deleted in order to prevent membrane anchoring. Typically, the signal sequence is positioned in the coding region of the S05A Peptide gene or cDNA, or directly at the 5' end of the Peptide gene coding region. Many signal sequences have been identified, and any of them that are functional in the selected host cell may be used in conjunction with the Peptide gene or cDNA. Therefore, the signal sequence may be homologous or heterologous to the Peptide gene or cDNA, and may be homologous or heterologous to the Peptide gene or cDNA. Additionally, the signal sequence may be chemically synthesized using methods set forth above. In most cases, secretion of the polypeptide from the host cell via the presence of a signal peptide will result in the removal of the amino terminal methionine from the polypeptide.

In many cases, transcription of the S05A Peptide gene or cDNA is increased by the presence of one or more introns in the vector; this is particularly true where the Peptide is produced in eukaryotic host cells, especially mammalian host cells. The introns used may be naturally occurring within the Peptide gene, especially where the gene used is a full length genomic sequence or a fragment thereof. Where the intron is not naturally occurring within the gene (as for most cDNAs), the intron(s) may be obtained from another source. The position of the intron with respect to the flanking sequence and the Peptide gene generally is important, as the intron must be transcribed to be effective. As such, where the Peptide gene inserted into the expression vector is a cDNA molecule, the preferred position for the intron is 3' to the transcription start site, and 5' to the polyA transcription termination sequence. Preferably for Peptide cDNA, the intron or introns will be located on one side or the other (i.e., 5' or 3') of the cDNA such that it does not interrupt this coding sequence. Any intron from any source, including any viral, prokaryotic and eukaryotic (plant or animal) organisms, may be used to practice this embodiment, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this embodiment may be constructed from starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to blunt the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra. Alternatively, two or more of the elements to be inserted into the vector may first be ligated together (if they are to be positioned adjacent to each other) and then ligated into the vector.

An additional method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this embodiment are those that are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15b (Novagen, Madison, Wis.), PGEX (Pharmacia Biotech, Piscataway, N.J.), pEGFP-N2 (Clontech, Palo Alto, Calif.), pETL (Blue-Bachl; Invitrogen), and pFastBacDual (Gibco/BRL, Grand Island, N.Y.).

After the vector has been constructed and a nucleic acid molecule encoding full length or truncated protein or peptide has been inserted into the proper site of the vector, the completed vector may be inserted into a suitable host cell for amplification and/or polypeptide expression. Host cells may be prokaryotic host cells (such as E. coli) or eukaryotic host cells (such as a yeast cell, an insect cell, or a vertebrate cell). The host cell, when cultured under appropriate conditions, can synthesize protein or peptide which can subsequently be collected from the culture medium (if the host cell secretes it into the medium) or directly from the host cell producing it (if it is not secreted).

After collection, the S05A Peptide can be purified using methods such as molecular sieve chromatography, affinity chromatography, and the like. Selection of the host cell for protein or peptide production will depend in part on whether the Peptide is to be glycosylated or phosphorylated (in which case eukaryotic host cells are preferred), and the manner in which the host cell is able to fold the Peptide into its native tertiary structure (e.g., proper orientation of disulfide bridges, etc.) such that biologically active protein is prepared by the Peptide that has biological activity, the Peptide may be folded after synthesis using appropriate chemical conditions as discussed below. Suitable cells or cell lines may be mammalian cells, such as Chinese hamster ovary cells (CHO), human embryonic kidney (HEK) 293, 293T cells, or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present embodiments are bacterial cells. For example, the various strains of *E. coli* (e.g., HB101, DH5.alpha., DH10, and MC1061) are well-known as host cells in the field of biotechnology. Various strains of *B. subtilis, Pseudomonas* spp., other *Bacillus* spp., *Streptomyces* spp., and the like may also be employed in this method. Many strains of yeast cells known to those skilled in the art also are available as host cells for expression of the polypeptides of the present embodiments.

Additionally, where desired, insect cell systems may be utilized in the methods of the present embodiments. Such systems are described for example in Kitts et al. (Biotechniques, 14:810-817), Lucklow (Curr. Opin. Biotechnol., 4:564-572) and Lucklow et al. (J. Virol., 67:4566-4579). Preferred insect cells are Sf-9 and Hi5 (Invitrogen, Carlsbad, Calif.).

Insertion (also referred to as transformation or transfection) of the vector into the selected host cell may be accomplished using such methods as calcium chloride, electroporation, microinjection, lipofection, or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary. Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of S05A Peptide produced in the host cell can be evaluated using standard methods known in the art. Such methods include, without limitation, Western blot analysis, SDS-polyacrylamide gel electrophoresis, non-denaturing gel electrophoresis, HPLC separation, mass spectroscopy, immunoprecipitation, and/or activity assays such as DNA binding gel shift assays.

If the protein or peptide has been designed to be secreted from the host cells, the majority of the protein or peptide may be found in the cell culture medium. Proteins prepared in this way will typically not possess an amino terminal methionine, as it is removed during secretion from the cell. If however, the protein or peptide is not secreted from the host cells, it will be present in the cytoplasm and/or the nucleus (for eukaryotic host cells) or in the cytosol (for gram negative bacteria host cells) and may have an amino terminal methionine.

For an S05A Peptide situated in the host cell cytoplasm and/or nucleus, the host cells are typically first disrupted mechanically or with detergent to release the intra-cellular contents into a buffered solution. The Peptide can then be isolated from this solution.

Purification of S05A Peptides from solution can be accomplished using a variety of techniques. If the S05A Peptide has been synthesized such that it contains a tag such as hexHistidine (SEQ ID NO: 9) (e.g. peptid/hexaHis (SEQ ID NO: 9)) or other small peptide such as FLAG (Sigma-Aldritch, St. Louis, Mo.) or calmodulin-binding peptide (Stratagene, La Jolla, Calif.) at either its carboxyl or amino terminus, it may essentially be purified in a one-step process by passing the solution through an affinity column where the column matrix has a high affinity for the tag or for the protein directly (i.e., a monoclonal antibody specifically recognizing the peptide). For example, polyhistidine binds with great affinity and specificity to nickel, zinc and cobalt; thus immobilized metal ion affinity chromatography which employs a nickel-based affinity resin (as used in Qiagen's QIAexpress system or Invitrogen's Xpress System) or a cobalt-based affinity resin (as used in BD Biosciences-CLONTECH's Talon system) can be used for purification of peptide/polyHis. (See, for example, Ausubel et al., eds., Current Protocols in Molecular Biology, Section 10.11.8, John Wiley & Sons, New York).

Where the S05A Peptide is prepared without a tag attached, and no antibodies are available, other well known procedures for purification can be used. Such procedures include, without limitation, ion exchange chromatography, hydroxyapatite chromatography, hydrophobic interaction chromatography, molecular sieve chromatography, HPLC, native gel electrophoresis in combination with gel elution, and preparative isoelectric focusing (Isoprime machine/technique, Hoefer Scientific). In some cases, two or more of these techniques may be combined to achieve increased purity.

If it is anticipated that the S05A Peptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation. If the Peptide has formed inclusion bodies in the cytosol, the inclusion bodies can often bind to the inner and/or outer cellular membranes and thus will be found primarily in the pellet material after centrifugation. The pellet material then can be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The Peptide in its now soluble form can then be analyzed using gel electrophoresis, immunoprecipitation or the like. If it is desired to isolate the Peptide, isolation may be accomplished using standard methods such as those set forth below and in Marston et al. Meth. Enz., 182:264-275.

In some cases, the S05A Peptide may not be biologically active upon isolation. Various methods for refolding or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. In most cases the refolding/oxidation solution will also contain a reducing agent or the reducing agent plus its, oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, 2-mercaptoethanol(bME)/dithio-b(ME). In many instances a cosolvent is necessary to increase the efficiency of the refolding and the more common reagents used for this purpose include glycerol, polyethylene glycol of various molecular weights, and arginine.

If S05A Peptide inclusion bodies are not formed to a significant degree in the host cell, the S05A Peptide will be found primarily in the supernatant after centrifugation of the cell homogenate, and the S05A Peptide can be isolated from the supernatant using methods such as those set forth below.

In those situations where it is preferable to partially or completely isolate the S05A Peptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying S05A Peptides using recombinant DNA techniques, the S05A Peptides and their fragments, variants, homologues, fusion proteins, peptide mimetics, and derivatives may be prepared by chemical synthesis methods (such as solid phase peptide synthesis) using techniques known in the art such as those set forth by Merrifield et al., J. Am. Chem. Soc., 85:2149, Houghten et al. Proc Natl Acad. Sci. USA, 82:5132, and Stewart and Young, Solid Phase Peptide Synthesis, Pierce Chemical Co., Rockford, Ill. Such Peptides may be synthesized with or without a methionine on the amino terminus. Chemically synthesized S05A Peptides may be oxidized using methods set forth in these references to form disulfide bridges. The S05A Peptides are expected to have biological activity comparable to Peptides produced recombinantly or purified from natural sources, and thus may be used interchangeably with recombinant or natural Peptide.

Chemically modified S05A Peptide compositions in which the Peptide is linked to a polymer are included within the scope of the present embodiments. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of peptide polymers is a mixture of polymers.

In some cases, it may be desirable to prepare nucleic acid and/or amino acid variants of the naturally occurring S05A Peptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Preferred nucleic acid variants are those containing nucleotide substitutions accounting for codon preference in the host cell that is to be used to produce S05A Peptides. Such codon optimization can be determined via computer algorithers which incorporate codon frequency tables such as Ecohigh. Cod for codon preference of highly expressed bacterial genes as provided by the University of Wisconsin Package Version 9.0, Genetics Computer Group, Madison, Wis. Other useful codon frequency tables include Celegans_high.cod, Celegans_low.cod, *Drosophila*_high.cod, Human_high.cod, Maize_high.cod, and Yeast_high.cod. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s), or those designed to delete an existing glycosylation and/or phosphorylation site(s).

S05A Peptides and fragments, homologs, variants, fusion proteins, peptide mimetics, derivatives and salts thereof also can be made using conventional peptide synthesis techniques known to the skilled artisan. These techniques include chemical coupling methods (cf. Wunsch, E: "Methoden der organischen Chemie", Volume 15, Band 1+2, Synthese von Peptiden, thime Verlag, Stuttgart (1974), and Barrany, G.; Marrifield, R. B.: "The Peptides," eds. E. Gross, J. Meienhofer, Volume 2, Chapter 1, pp. 1-284, Academic Press (1980)), enzymatic coupling methods (cf. Widmer, F. Johansen, J. T., Carlsberg Res. Commun., Vol. 44, pp. 37-46 (1979); Kullmann, W.: "Enzymatic Peptide Synthesis", CRC Press Inc. Boca Raton, Fla. (1987); and Widmer, F., Johansen, J. T. in "Synthetic Peptides in Biology and Medicines," eds. Alitalo, K., Partanen, P., Vatieri, A., pp. 79-86, Elsevier, Amsterdam (1985)), or a combination of chemical and enzymatic methods if this is advantageous for the process design and economy. Using the guidelines provided herein, those skilled in the art are capable of varying the peptide sequence of the S05A Peptide to make a homologue having the same or similar biological activity (bioactivity) as the original or native S05A Peptide.

Advantages exist for using a mimetic of a given S05A Peptide rather than the Peptide itself. In general, peptide mimetics are more bioavailable, have a longer duration of action and can be cheaper to produce than the native proteins and peptides.

Thus the peptides described above have utility in the development of such small chemical compounds with similar biological activities and therefore with similar therapeutic utilities. Peptide mimetics of S05A Peptides can be developed using combinatorial chemistry techniques and other techniques known in the art (see e.g. Proceedings of the 20th European Peptide Symposium, ed. G. Jung, E. Bayer, pp. 289-336, and references therein).

Examples of methods known in the art for structurally modifying a peptide to create a peptide mimetic include the inversion of backbone chiral centers leading to D-amino acid residue structures that may, particularly at the N-terminus, lead to enhanced stability for proteolytical degradation without adversely affecting activity. An example is provided in the paper "Tritriated D-ala.sup.1-Peptide T Binding", Smith C. S. et al., Drug Development Res. 15, pp. 371-379 (1988).

A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety.

A third method is to substitute peptide bonds in the S05A Peptide by pseudopeptide bonds that confer resistance to proteolysis. A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of the peptides described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus.

The synthesis of peptides with one or more reduced retro-inverso pseudopeptide bonds is known in the art (Sisto (1990) and Dalpozzo, et al. (1993), cited above). Thus, peptide bonds can be replaced by non-peptide bonds that allow the peptide mimetic to adopt a similar structure, and therefore biological activity, to the original peptide. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond is a (Couder, et al. (1993), Int. J. Peptide Protein Res., 41:181-184, incorporated herein by reference in its entirety). Thus, the amino acid sequences of these peptides may be identical to the sequences of an peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of S05A Peptides represent another class of peptide mimetics that retain the important structural determinants for biological activity, yet eliminate the peptide bonds, thereby conferring resistance to proteolysis (Simon, et al., 1992, Proc. Natl. Acad. Sci. USA, 89:9367-9371 and incorporated herein by reference in its entirety). Peptoids are oligomers of N-substituted glycines. A number of N-alkyl groups have been described, each corresponding to the side chain of a natural amino acid (Simon, et al. (1992), cited above and incorporated herein by reference in its entirety). Some or all of the amino acids of the peptide are replaced with the N-substituted glycine corresponding to the replaced amino acid.

The development of peptide mimetics can be aided by determining the tertiary structure of the original peptide by NMR spectroscopy, crystallography and/or computer-aided molecular modeling. These techniques aid in the development of novel compositions of higher potency and/or greater bioavailability and/or greater stability than the original peptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference in their entirety).

Once a potential peptide mimetic compound is identified, it may be synthesized and assayed using the methods outlined in the examples below to assess its activity. The peptide mimetic compounds obtained by the above methods, having the biological activity of the peptides and similar three-dimensional structure, are encompassed by this embodiment. It will be readily apparent to one skilled in the art that a peptide mimetic can be generated from any of the peptides bearing one or more of the modifications described above. It will furthermore be apparent that the peptide mimetics of this embodiment can be further used for the development of even more potent non-peptidic compounds, in addition to their utility as therapeutic compounds.

A number of organizations exist today that are capable of synthesizing the peptides described herein. For example, given the sequence of an S05A Peptide, the organization can synthesize the Peptide and forward the synthesized Peptide with accompanying documentation and proof of the identity of the Peptide.

Embodiments also encompasses the use of S05A Peptides and their corresponding nucleic acid molecules for assays to test, either qualitatively or quantitatively, for the presence of S05A Peptides, S05A Peptide DNA, or corresponding RNA in mammalian tissue or bodily fluid samples. S05A Peptides and their corresponding nucleic acid molecules may have use in the preparation in such assays, whether or not the Peptide or the encoded Peptide DNA show biological activity. S05A Peptide nucleic acid sequences may be a useful source of hybridization probes to test, either qualitatively or quantitatively, for the presence of Peptide DNA or corresponding RNA in mammalian tissue or bodily fluid samples. S05A Peptides which is not in itself biologically active may be useful for preparing antibodies that recognize and/or bind to S05A Peptides. Such antibodies may be prepared using standard methods. Thus, antibodies that react with or bind to the S05A Peptides, as well as short chain antibody fragments and other reactive fragments of such antibodies, also are contemplated as within the scope of the present embodiments. The antibodies may be polyclonal, monoclonal, recombinant, chimeric, single-chain and/or bispecific. Typically, the antibody or fragment thereof will either be of human origin, or will be humanized, i.e., prepared so as to prevent or minimize an immune reaction to the antibody when administered to a patient. Preferred antibodies are human antibodies, either polyclonal or monoclonal. The antibody fragment may be any fragment that is reactive with peptides of the present embodiments, such as, Fab, Fab', etc. Also provided by this embodiment are the hybridomas generated by presenting any S05A Peptide as an antigen to a selected mammal, followed by fusing cells (e.g., spleen cells) of the mammal with certain cancer cells to create immortalized cell lines by known techniques. The methods employed to generate such cell lines and antibodies directed against all or portions of an S05A Peptide are also encompassed by the embodiments.

The antibodies may further be used for in vivo and in vitro diagnostic or research purposes, such as in labeled form to detect the presence of an S05A Peptide in a body fluid or cell sample.

The embodiments also encompasses the use of one or more S05A Peptides as calibration standards in assays that test, either qualitatively or quantitatively, for the presence of S05A Peptides, proteins, Peptide DNA, protein DNA, or corresponding RNA in mammalian tissue or bodily fluid samples.

The present embodiments are directed to methods of treating conditions requiring removal of cells, such as benign and malignant tumors, glandular (e.g. prostate) hyperplasia, unwanted facial hair, warts, and unwanted fatty tissue, or the inhibition or prevention of unwanted cellular proliferation, such as stenosis of a stent. Such a method comprises administering to a mammal in need, or coating a device such as a stent with, a therapeutically effective amount of S05A Peptide.

The condition can be, for example, tumors of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, lymph nodes and lymphoid system, and other organs.

As used herein, the term "malignant tumor" is intended to encompass all forms of human carcinomas, sarcomas and melanomas which occur in the poorly differentiated, moderately differentiated, and well-differentiated forms.

This embodiment satisfies a need in the art for treatments that can remove benign tumors with less risk and fewer of the undesirable side effects of surgery. A method for removing benign tumors in surgically hazardous areas such as in deep locations in the body (e.g., brain, heart, lungs, and others) is particularly needed.

The method of treating conditions where cells must be removed can be used in conjunction with conventional methods of treating such conditions, such as surgical excision, chemotherapy, and radiation. peptides can be administered before, during, or after such conventional treatments.

The condition to be treated can also be a hyperplasia, hypertrophy, or overgrowth of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

Other conditions that can be treated using the method of the embodiments are virally, bacterially, or parasitically altered tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

The condition to be treated can also be a malformation or disorder of a tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

In particular, the condition to be treated can be tonsillar hypertrophy, prostatic hyperplasia, psoriasis, eczema, dermatoses or hemorrhoids. The condition to be treated can be a vascular disease, such as atherosclerosis or arteriosclerosis, or a vascular disorder, such as varicose veins, stenosis or restenosis of an artery or a stent. The condition to be treated can also be a cosmetic modification to a tissue, such as skin, eye, ear, nose, throat, mouth, muscle, connective tissue, hair, or breast tissue.

Therapeutic compositions of S05A Peptides also are contemplated in the present embodiments. Such compositions may comprise a therapeutically effective amount of an S05A Peptide in admixture with a pharmaceutically acceptable carrier. The carrier material may be water for injection, preferably supplemented with other materials common in solutions for administration to mammals. Typically, an S05A Peptide for therapeutic use will be administered in the form of a composition comprising purified peptide in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Compositions of the embodiments also may comprise buffers known to those having ordinary skill in the art with an appropriate range of pH values, including Tris buffer of about pH 7.0-8.5, or acetate buffer of about pH 4.0-5.5, which may further include sorbitol or a suitable substitute therefor.

The use of S05A Peptides conjugated or linked or bound to an antibody, antibody fragment, antibody-like molecule, or a molecule with a high affinity to a specific tumor marker, such as a cellular receptor, signal peptide or over-expressed enzyme, for targeting to the unwanted cellular elements also is encompassed by the scope of the embodiments. The antibody, antibody fragment, antibody-like molecule, or molecule with a high affinity to a specific tumor marker is used to target the Peptide conjugate to a specific cellular or tissue target. For example, a tumor with a distinctive surface antigen or expressed antigen can be targeted by the antibody, antibody fragment, or antibody-like binding molecule and the tumor cells can be killed by the Peptide. Such an approach using antibody targeting has the anticipated advantages of decreasing dosage, increasing the likelihood of binding to and uptake by the target cells, and increased usefulness for targeting and treating metastatic tumors and microscopic sized tumors.

This embodiment also encompasses the use of S05A Peptides conjugated or linked or bound to a protein or other molecule to form a composition that, upon cleavage at or near the site(s) of the tumor or other unwanted cells by a tumor- or site-specific enzyme or protease or by an antibody conjugate that targets tumor or other unwanted cells, releases the Peptide at or near the site(s) of the tumor or other unwanted cells This embodiment also encompasses the use of S05A Peptides conjugated or linked or bound to a protein or other molecule to form a composition that releases the Peptide or some biologically active fragment of the Peptide upon exposure of the tissue to be treated to light (as in laser therapies or other photo-dynamic or photo-activated therapy), other forms of electromagnetic radiation such as infra-red radiation, ultraviolet radiation, x-ray or gamma ray radiation, localized heat, alpha or beta radiation, ultrasonic emissions, or other sources of localized energy.

The S05A Peptides may be employed alone, together, or in combination with other pharmaceutical compositions, such as cytokines, growth factors, antibiotics, apoptotis-inducing agents, anti-inflammatories, and/or chemotherapeutic agents as is appropriate for the indication being treated.

This embodiment also encompasses therapeutic compositions of S05A Peptides employing dendrimers, fullerenes, and other synthetic molecules, polymers and macromolecules where the Peptide and/or its corresponding DNA molecule is conjugated with, attached to or enclosed in the molecule, polymer or macromolecule, either by itself or in conjunction with other species of molecule such as a tumor-specific marker. For example, U.S. Pat. No. 5,714,166, Bioactive and/or Targeted Dendimer Conjugates, provides a method of preparing and using, inter alia, dendritic polymer conjugates composed of at least one dendrimer with a target director(s) and at least one bioactive agent conjugated to it. The disclosure of U.S. Pat. No. 5,714,166 is incorporated by reference herein in its entirety.

This embodiment also encompasses therapeutic compositions of S05A Peptides and/or genes and drug delivery vehicles such as lipid emulsions, micelle polymers, polymer microspheres, electroactive polymers, hydrogels and liposomes.

The use of S05A Peptides or related genes or gene equivalents transferred to the unwanted cells also is encompassed by the embodiments. Overexpression of Peptide within the tumor can be used to induce the cells in the tumor to die and thus reduce the tumor cell population. The gene or gene equivalent transfer of S05A Peptide to treat the unwanted cellular elements is anticipated to have the advantage of requiring less dosage, and of being passed on to the cellular progeny of the targeted cellular elements, thus necessitating less frequent therapy, and less total therapy. This embodiment also encompasses the transfer of genes that code for a fusion protein containing an S05A Peptide to the unwanted cells or neighboring cells where, following the expression of the gene and the production and/or secretion of the fusion protein, the fusion protein is cleaved either by native enzymes or proteases or by a prodrug to release the Peptide in, at or near the unwanted cells.

The use of cloned recombinant peptide-antibody conjugates; cloned recombinant peptide-antibody fragment conjugates; and cloned recombinant peptide-antibody-like protein conjugates is also encompassed by the scope of the embodiments. The advantages of a cloned S05A Peptide combined with targeting conjugate (such as an antibody, antibody fragment, antibody-like molecule, or a molecule with a high affinity to a cancer-specific receptor or other tumor marker) are that such a molecule combines the targeting advantages described above in addition to advantages for manufacturing and standardized production of the cloned conjugated molecule.

This embodiment also encompasses the use of therapeutic compositions of S05A Peptides or genes or gene equivalents as a component of the coating of a medical device such as a stent in order to remove, inhibit or prevent unwanted cellular proliferation or accumulation.

Solid dosage forms for oral administration include but are not limited to, capsules, tablets, pills, powders, and granules. In such solid dosage forms, the active compound is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the compositions of the embodiments may be varied to obtain an amount of S05A Peptide that is effective to obtain a desired therapeutic response for a particular composition and method of administration. The selected dosage level therefore depends upon the desired therapeutic effect, the route of administration, the desired duration of treatment, and other factors.

With mammals, including humans, the effective amounts can be administered on the basis of body surface area. The interrelationship of dosages for animals of various sizes, species and humans (based on mg/M.sup.2 of body surface) is described by E. J. Freireich et al., Cancer Chemother. Rep., 50 (4):219 (1966). Body surface area may be approximately determined from the height and weight of an individual (see e.g., Scientific Tables, Geigy Pharmaceuticals, Ardsley, N.Y. pp. 537-538 (1970)).

The total daily dose of the S05A Peptide administered to a host may be in single or divided doses. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

A method of administering an S05A Peptide composition according to the embodiments includes, but is not limited to, administering the compounds intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc.

Another method of administering an S05A Peptide of the embodiments is by a transdermal or transcutaneous route. One example of such an embodiment is the use of a patch. In particular, a patch can be prepared with a fine suspension of Peptide in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the Peptide compound in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

S05A Peptides may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., Biopolymers, 22: 547-556), poly(2-hydroxyethyl-methacrylate) (Langer et al., J. Biomed. Mater. Res., 15: 167-277 and Langer, Chem. Tech., 12: 98-105), ethylene vinyl acetate (Langer et al., supra) or poly-D(−)-3-hydroxy-butyric acid (EP 133,988). Sustained-release compositions also may include liposomes, which can be prepared by any of several methods known in the art (e.g., Eppstein et al., Proc. Natl. Acad. Sci. USA, 82: 3688-3692; EP 36,676; EP 88,046; and EP 143,949).

Another method of administering an S05A Peptide of the embodiments is by direct or indirect infusion of Peptide into the tumor or other tissue to be treated. One example of such an embodiment is the direct injection of Peptide into the tumor or other tissue to be treated. The treatment may consist of a single injection, multiple injections on one occasion or a series of injections over a period of hours, days or months with the regression or destruction of the tumor or other tissue to be treated being monitored by means of biopsy, imaging or other methods of monitoring tissue growth. The injection into the tumor or other tissue to be treated may be by a device inserted into an orifice such as the nose, mouth, ear, vagina, rectum or urethra or through an incision in order to reach the tumor or tissue in vivo and may performed in conjunction with an imaging or optical system such as ultrasound or fibre optic scope in order to identify the appropriate site for the injection(s). Another example of such an embodiment is the use of a device that can provide a constant infusion of S05A Peptide to the tissue over time.

Another method of administering an S05A Peptide of the embodiments is in conjunction with a surgical or similar procedure employed to physically excise, ablate or otherwise kill or destroy tumor or other tissue or cellular elements required or desired to be removed or destroyed wherein an S05A Peptide of the embodiments is administered to the immediate area(s) surrounding the area(s) where the tumor or other tissue was removed in order to destroy or impede the growth of any tumor cells or other cellular elements not removed or destroyed by the procedure Another method of administering an S05A Peptide of the embodiments is by implantation of a device within the tumor or other tissue to be treated. One example of such an embodiment is the implantation of a wafer containing Peptide in the tumor or other tissue to be treated. The wafer releases a therapeutic dose of Peptide into the tissue over time. Alternatively or additionally, the composition may be administered locally via implantation into the affected area of a membrane, sponge, or other appropriate material on to which the S05A Peptide has been absorbed. Where an implantation device is used, the device may be implanted into any suitable tissue or organ, and delivery of the Peptide may be directly through the device via bolus, or via continuous administration, or via catheter using continuous infusion.

An alternative method of administration is to introduce one or more copies of an S05A Peptide-encoding gene into the cell being targeted and, if necessary, inducing the copy(ies) of the gene to begin producing Peptide intracellularly. One manner in which gene therapy can be applied is to use the S05A Peptide-encoding gene (either genomic DNA, cDNA, and/or synthetic DNA encoding the Peptide (or a fragment, variant, homologue or derivative thereof)) which may be operably linked to a constitutive or inducible promoter to form a gene therapy DNA construct. The promoter may be homologous or heterologous to an endogenous Peptide-encoding gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

Means of gene delivery to a cell or tissue in vivo or ex vivo include (but are not limited to) direct injection of bare DNA, ballistic methods, liposome-mediated transfer, receptor-mediated transfer (ligand-DNA complex), electroporation, and calcium phosphate precipitation. See U.S. Pat. No. 4,970, 154, WO 96/40958, U.S. Pat. Nos. 5,679,559, 5,676,954, and 5,593,875, the disclosures of each of which are incorporated by reference herein in their entirety. They also include use of a viral vector such as a retrovirus, adenovirus, adeno-associated virus, pox virus, lentivirus, papilloma virus or herpes simplex virus, use of a DNA-protein conjugate and use of a liposome. The use of gene therapy vectors is described, for example, in U.S. Pat. Nos. 5,672,344, 5,399,346, 5,631,236, and 5,635,399, the disclosures of each of which are incorporated by reference herein in their entirety.

The S05A Peptide-encoding gene may be delivered through implanting into patients certain cells that have been genetically engineered ex vivo, using methods such as those described herein, to express and secrete the S05A Peptide or fragments, variants, homologues, or derivatives thereof. Such cells may be animal or human cells, and may be derived from the patient's own tissue or from another source, either human or non-human. Optionally, the cells may be immortalized or be stem cells. However, in order to decrease the chance of an immunological response, it is preferred that the cells be encapsulated to avoid infiltration of surrounding tissues. The encapsulation materials are typically biocompatible, semipermeable polymeric enclosures or membranes that allow release of the protein product(s) but prevent destruction of the cells by the patient's immune system or by other detrimental factors from the surrounding tissues. Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627, the disclosures of each of which are incorporated by reference herein in their entirety. A system for encapsulating living cells is described in PCT WO 91/10425. Techniques for formulating a variety of other sustained or controlled delivery means, such as liposome carriers, bioerodible particles or beads, are also known to those in the art, and are described, for example, in U.S. Pat. No. 5,653,975, the disclosure of which is incorporated by reference herein in their entirety. The cells, with or without encapsulation, may be implanted into suitable body tissues or organs of the patient.

Particularly preferred embodiments of methods of treating a disorder requiring the removal or destruction of cells administering one or more peptides of the embodiments, and the cells to be removed or destroyed are present lymphoid tissue. Other preferred embodiments include treating conditions that require removal or destruction of cells such as any one selected from individually or in combination tonsillary hypertrophy, prostatic hyperplasia, vascular disease (atherosclerosis or arteriosclerosis), hemorrhoids, varicose veins, psoriasis, eczema, dermatosis, and a cosmetic modification to a tissue. Other treatable conditions include stenosis, restenosis, occlusion or blockage of an artery or of a stent placed or implanted in an artery. Suitable tissue that can be treated in the preferred embodiments include skin, eye, ear, nose, throat, mouth, muscle, connective, hair, and breast.

Other preferred conditions treated in accordance with the embodiments include those selected from an inflammatory disease, autoimmune disease, metabolic disease, hereditary/genetic disease, traumatic disease or physical injury, nutritional deficiency disease, infectious disease, amyloid disease, fibrosis disease, storage disease, congenital malformation, enzyme deficiency disease, poisoning, intoxication, environmental disease, radiation disease, endocrine disease, degenerative disease and mechanical disease. In another preferred embodiment, the peptide is conjugated, linked, or bound to a molecule selected from an antibody, antibody fragment, and an antibody-like binding molecule, wherein said molecule has a higher affinity for binding to a tumor or other target than binding to other cells. In another embodiment, the peptide is part of a single new cloned recombinant molecule consisting of the peptide and a molecule selected from the group consisting of an antibody, antibody fragment, and antibody-like binding molecule, wherein the molecule has a higher affinity for binding to a tumor or other target than binding to other cells.

The following examples are provided to illustrate the present embodiments. It should be understood, however, that the embodiments are not to be limited to the specific conditions or details described in these examples. Throughout the specification, any and all references to a publicly available document, including a U.S. patent, are specifically incorporated by reference.

In particular, the embodiments expressly incorporate by reference the examples contained in pending U.S. patent application Ser. No. 10/092,934, Methods of Treating Tumors and Related Conditions Using Neural Thread Proteins, which reveal that the whole AD7c-protein is an effective agent for causing cell death both in vitro in glioma and neuroblastoma cell cultures and in vivo in normal rodent muscle tissue, subcutaneous connective tissue, and dermis and in a variety of different human and non-human origin tumors, including mammary carcinoma, skin carcinoma and papilloma, colon carcinoma, glioma of brain, and others in rodent models. The embodiments also expressly incorporates by reference the examples contained in pending U.S. patent application Ser. No. 10/153,334, entitled: Peptides Effective In The Treatment Of Tumors And Other Conditions Requiring The Removal Or Destruction Of Cells; Ser. No. 10/198,069, entitled: Peptides Effective In The Treatment Of Tumors And Other Conditions Requiring The Removal Or Destruction Of Cells; Ser. No. 10/198,070, entitled: Peptides Effective In The Treatment Of Tumors And Other Conditions Requiring The Removal Or Destruction Of Cells, Ser. No. 10/294,891 entitled: Peptides Effective In The Treatment Of Tumors And Other Conditions Requiring The Removal Or Destruction Of Cells; and Ser. No. 10/920,313 entitled: Peptides Effective In The Treatment Of Tumors And Other Conditions Requiring The Removal Or Destruction Of Cells, each of which reveal that certain peptides specified therein are effective agents for causing cell death in vivo in normal rodent muscle tissue, subcutaneous connective tissue, dermis and other tissue.

EXAMPLE 1

The purpose of this example was to determine the effect of S05A Peptides on tissue at sites of injection.

The following S05A Peptides were synthesized using standard methods:

```
S05A-2
                                      (SEQ ID NO. 2)
IDQQVLSRI (Ile-Asp-Gln-Gln-Val-Leu-Ser-Arg-Ile);

S05A-3
                                      (SEQ ID NO. 3)
KLEIKRCL (Lys-Leu-Glu-Ile-Lys-Arg-Cys-Leu);

S05A-4
                                      (SEQ ID NO. 4)
VLSRIK (Val-Leu-Ser-Arg-Ile-Lys);

S05A-5
                                      (SEQ ID NO. 5)
RIKLEIK (Arg-Ile-Lys-Leu-Glu-Ile-Lys);

S05A-6
                                      (SEQ ID NO. 6)
VLSRIKLEIKRCL (Val-Leu-Ser-Arg-Ile-Lys-Leu-Glu-

Ile-Lys-Arg-Cys-Leu);

S05A-7
                                      (SEQ ID NO. 7)
IDQQVLSRIKLEI (Ile-Asp-Gln-Gln-Val-Leu-Ser-Arg-

Ile-Lys-Leu-Glu-Ile).
```

Male Sprague-Dawley rats (300 gram weight range) were anesthetized with ether and given one of the above S05A Peptides by intraprostatic infusion, a control injection of normal saline or no injection after open surgical visualization of the prostate. The injections consisted of 300 μl of the S05A Peptide 1 mg/mL in PBS pH 7.4. (1.0 mg/kg) (n=36). Rats were painlessly sacrificed after 24 hours (n=12), 72 hours (n=12) and 7 days (n=12). Prostate glands were dissected, fixed in 10% buffered formalin for 24 hours, embedded in paraffin, sectioned, and stained with H & E. For each animal the entire prostate gland was embedded and sectioned. All stained sections were examined histologically and measured. For each prostate at least 2 histological sections were examined, and for each histological section two cross-sectional diameters (D) at 90° from each other were measured (total of ≧8 measurements per prostate). The mean of the cross-sectional diameters (D) for each group was used to estimate volume according to $V=4/3\pi(D/2)^3$ and the mean volume calculated for each group. Histological changes were assessed on the following scale:
- − Absent
- + Present, Minimal
- ++ Present, Moderate
- +++ Present, Moderate and Diffuse
- ++++ Present, Diffuse and Extensive Results: Table 4 below sets out the histological changes of cell death observed.

TABLE 4

| S05A Peptide | Histological Changes of Cell Death at 24 Hours | Histological Changes of Cell Death at 72 Hours |
|---|---|---|
| S05A-2 | ++++ | ++++ |
| S05A-3 | + | + |
| S05A-4 | + | + |
| S05A-5 | + | + |
| S05A-6 | + | + |
| S05A-7 | ++++ | ++++ |

Previous control studies of injections of 1 mg/mL PBS alone showed absent or minimal histological changes, consisting of mild focal inflammation from the needles (see the examples contained in pending U.S. patent application Ser. No. 10/153,334, entitled: Peptides Effective In The Treatment Of Tumors And Other Conditions Requiring The Removal Or Destruction Of Cells; Ser. No. 10/198,069, entitled: Peptides Effective In The Treatment Of Tumors And Other Conditions Requiring The Removal Or Destruction Of Cells; Ser. No. 10/198,070, entitled: Peptides Effective In The Treatment Of Tumors And Other Conditions Requiring The Removal Or Destruction Of Cells, Ser. No. 10/294,891 entitled: Peptides Effective In The Treatment Of Tumors And Other Conditions Requiring The Removal Or Destruction Of Cells; and Ser. No. 10/920,313 entitled: Peptides Effective In The Treatment Of Tumors And Other Conditions Requiring The Removal Or Destruction Of Cells, incorporated by reference).

Table 5 below sets out the volume changes observed.

TABLE 5

| S05A Peptide | Calculated Mean Volume (mm$^3$) | | | |
|---|---|---|---|---|
| | 24 Hours | 72 Hours | 7 Days | Overall |
| S05A-2 | 180 | 249 | 165 | 198 |
| S05A-3 | 249 | 435 | 463 | 382 |
| S05A-4 | 357 | 408 | 333 | 366 |
| S05A-5 | 249 | 408 | 392 | 350 |
| S05A-6 | 310 | 493 | 408 | 404 |
| S05A-7 | 180 | 165 | 357 | 234 |

The overall reduction in prostate volume in So5A Peptides S05A-2 and S50A-7 injected rats was estimated to be on average >40% compared to controls. Rats treated with S50A-2 and S50A-7 showed extensive cell death, necrosis, loss of glandular epithelium and atrophy. Controls showed minimal or absent changes consisting of acute inflammation at the injection sites and focal microhemorrhages from the needles.

It will be apparent to those skilled in the art that various modifications and variations can be made in the methods and compositions of the present embodiments without departing from the spirit or scope of the embodiments.

What is claimed is:

1. An isolated peptide selected from the group consisting of:
a) the peptide consisting of the amino acid sequence in SEQ ID NO. 2 (Ile-Asp-Gln -Gln-Val-Leu-Ser-Arg-Ile);
b) the peptide consisting of the amino acid sequence in SEQ ID NO. 3 (Lys-Leu -Glu-Ile-Lys-Arg-Cys-Leu);
c) the peptide consisting of the amino acid sequence in SEQ ID NO. 4 (Val-Leu-Ser -Arg-Ile-Lys);
d) the peptide consisting of the amino acid sequence in SEQ ID NO. 5 (Arg-Ile-Lys -Leu-Glu-Ile-Lys);
e) the peptide consisting of the amino acid sequence in SEQ ID NO. 6 (Val-Leu-Ser -Arg-Ile-Lys-Leu-Glu-Ile-Lys-Arg-Cys-Leu); and
f) the peptide consisting of the amino acid sequence in SEQ ID NO. 7 (Ile-Asp-Gln -Gln-Val-Leu-Ser-Arg-Ile-Lys-Leu-Glu-Ile).

2. A composition comprising at least one of the peptides as claimed in claim 1 and a carrier.

3. The isolated peptide of claim 1 optionally fused to an antibody, fragment of an antibody or an antibody-like molecule.

4. The isolated peptide of claim 1 optionally further modified with at least one and up to 25 additional amino acids flanking either the N-terminus or C-terminus of the peptide of claim 2, wherein the said isolated peptide does not comprise the amino acid sequence in SEQ ID NO. 1 (Ile-Asp-Gln-Gln-Val-Leu-Ser-Arg-Ile-Lys-Leu-Glu-Ile-Arg-Cys-Leu).

* * * * *

SEQUENCE LISTING

```
<160> NUMBER OF SEQ ID NOS: 9

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Asp Gln Gln Val Leu Ser Arg Ile Lys Leu Glu Ile Lys Arg Cys
 1               5                  10                  15

Leu

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Asp Gln Gln Val Leu Ser Arg Ile
 1               5

<210> SEQ ID NO 3
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Leu Glu Ile Lys Arg Cys Leu
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Ser Arg Ile Lys
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ile Lys Leu Glu Ile Lys
 1               5

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Leu Ser Arg Ile Lys Leu Glu Ile Lys Arg Cys Leu
 1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Asp Gln Gln Val Leu Ser Arg Ile Lys Leu Glu Ile
 1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Thr Glu Ser His
 1               5
```

```
<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
  1               5
```